United States Patent [19]

Brand et al.

[11] 4,453,001

[45] Jun. 5, 1984

[54] ISOXAZOLYL INDOLAMINES AS INTERMEDIATES

[75] Inventors: Leonard J. Brand, Randolph; Jeffrey Nadelson, Denville, both of N.J.

[73] Assignee: Sandoz, Inc., E. Hanover, N.J.

[21] Appl. No.: 524,995

[22] Filed: Aug. 22, 1983

Related U.S. Application Data

[60] Division of Ser. No. 351,187, Feb. 22, 1982, which is a division of Ser. No. 196,784, Oct. 14, 1980, Pat. No. 4,336,378, which is a continuation-in-part of Ser. No. 138,873, Apr. 10, 1980, abandoned.

[51] Int. Cl.³ .................. C07D 261/06; C07D 209/04
[52] U.S. Cl. .................................... 548/466; 548/504
[58] Field of Search .................. 548/504, 466, 247; 544/137, 367; 546/201

[56] References Cited

U.S. PATENT DOCUMENTS 4,336,378 6/1972 Brand et al. ........................ 544/137

OTHER PUBLICATIONS

Mirsky, et al., "Insulinase Inhibitory Actions . . . ," *Chem. Abst.* 51: 15775(d) (1957).
Spector, Merrill; "Reduction 3–Indolylcarbonyl Compounds . . . " *Chem. Abst.* 52: 12923(f) (1958).
Mashkovskii et al., "Pharm. Study of Tryptamine . . . " *Chem. Abst.* 81: 9606(g) (1974).
Smith, et al., "Hypoglycemic Action of Tryptamine," *Chem. Abst.* 87: 16491t (1977).

*Primary Examiner*—Donald G. Daus
*Assistant Examiner*—G. M. Hendricks
*Attorney, Agent, or Firm*—Gerald D. Sharkin; Robert S. Honor; Richard E. Vila

[57] ABSTRACT

This disclosure describes compounds of the formula

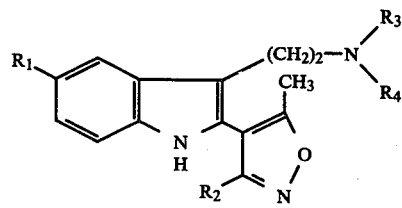

wherein
$R_1$ represents hydrogen, fluoro, chloro, lower alkyl having 1 to 4 carbon atoms, or lower alkoxy having 1 to 4 carbon atoms, and
$R_2$ represents lower alkyl or

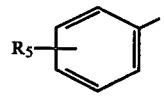

where $R_5$ represents hydrogen, fluoro, chloro, lower alkyl or lower alkoxy, and
$R_3$ and $R_4$ each independently represent lower alkyl as defined above, and
$R_3$ and $R_4$ together with N represent

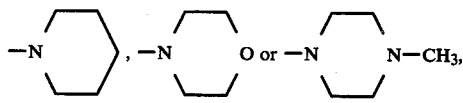

or pharmaceutically acceptable acid addition salts thereof, which are useful as anti-diabetic agents.

3 Claims, No Drawings

ISOXAZOLYL INDOLAMINES AS INTERMEDIATES

This is a division of application Ser. No. 351,187, filed Feb. 22, 1982 which in turn is a division of application Ser. No. 196,784, filed Oct. 14, 1980, now U.S. Pat. No. 4,336,378, which in turn is a continuation-in-part of Ser. No. 138,873, filed Apr. 10, 1980, now abandoned.

This invention relates to substituted isoxazolyl indolamines which exhibit anti-diabetic activity. In particular, it relates to 2-(5-methyl-3-substituted-4-isoxazolyl)-3-substituted-indoles and pharmaceutically acceptable acid addition salts.

The compounds of this invention may be represented by the following structural formula

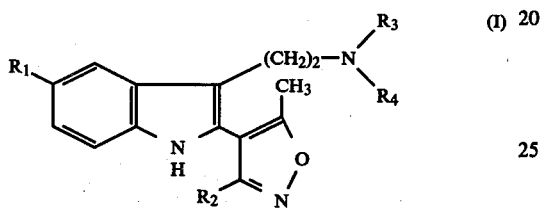
(I)

wherein $R_1$ represents hydrogen, fluoro, chloro, lower alkyl, i.e., alkyl having 1 to 4 carbon atoms, e.g., methyl, ethyl, isopropyl and the like, or lower alkoxy, i.e., alkoxy having 1 to 4 carbon atoms, e.g., methoxy, ethoxy, and the like, and $R_2$ represents lower alkyl, i.e., alkyl having 1 to 4 carbon atoms, e.g., methyl, ethyl and the like or

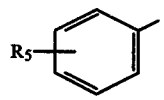

where $R_5$ represents hydrogen, fluoro, chloro, lower alkyl as defined above or lower alkoxy as defined above, and $R_3$ and $R_4$ each independently represent lower alkyl as defined above, and $R_3$ and $R_4$ together with N represent

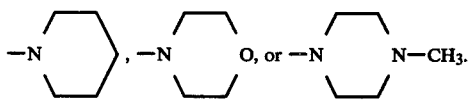

The compounds of formula (I) in which $R_2$ represents

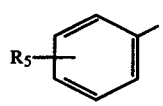

are prepared according to the following reation scheme:

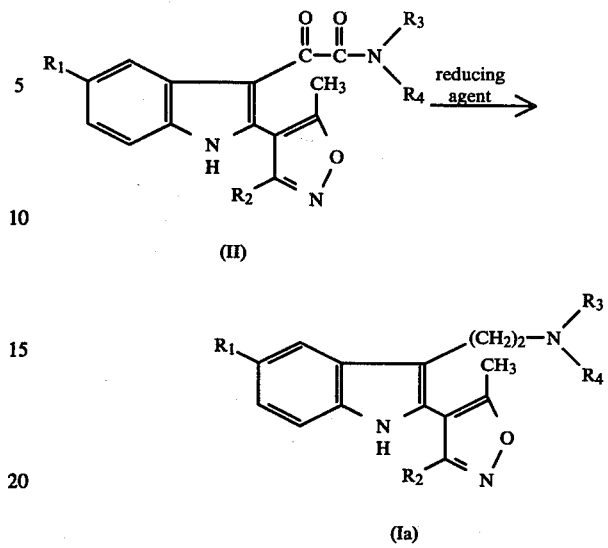

where $R_1$, $R_2$, $R_3$ and $R_4$ are as defined above.

The compounds of formula (Ia) are prepared by reducing a compound of the formula (II) in the presence of an inert atmosphere, e.g., nitrogen, helium or argon, preferably nitrogen, and an alkali metal hydride reducing agent such as sodium borohydride, lithium aluminum hydride, and the like, preferably lithium aluminum hydride. The reaction is carried out in the presence of an inert organic solvent, and although the particular solvent employed is not critical, the preferred solvents include an ether such as diethylether, dioxane or tetrahydrofuran, the latter being especially preferred. The temperature of the reaction is not critical, but it is preferred that the reaction be run at a temperature of from about 60° to 150° C., preferably the reflux temperature of the solvent. The reaction is run from about 1 to 12 hours, preferably from about 2 to 5 hours. The product is recovered using conventional techniques, e.g., crystallization.

The compounds of formula (II) are prepared according to the following reaction scheme:

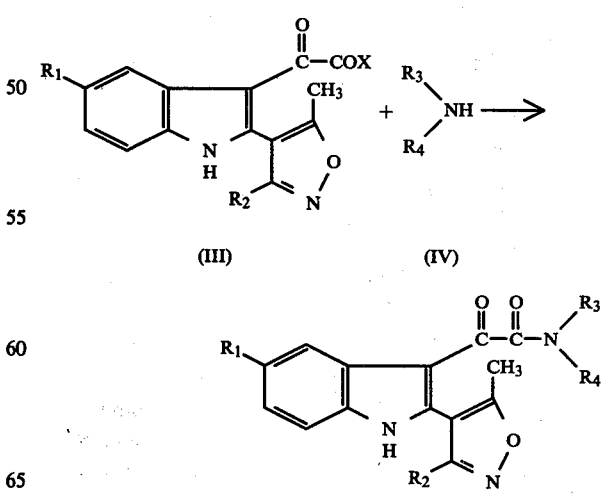

where X represents chloro or bromo, and $R_1$, $R_2$, $R_3$ and $R_4$ are as defined above.

The compounds of formula (II) are prepared by treating a compound of the formula (III) with a compound of the formula (IV) in the presence of an inert organic solvent. Although the particular solvent employed is not critical, the preferred solvents include water and an excess of a compound of the formula (IV) or an ether such as diethylether dioxane or tetrahydrofuran, or an aromatic hydrocarbon such as benzene, toluene and the like, preferably, however, the combination of water and an excess of a compound of the formula (IV) together with diethylether. The temperature of the reaction is not critical, but is preferred that the reaction be run from about $-10°$ to $50°$ C., preferably from about $20°$ to $30°$ C. The reaction is run from about 30 minutes to 4 hours, preferably from about 1 to 2 hours. The product is recovered using conventional techniques, e.g., filtration.

The compounds of formula (III) are prepared in accordance with the following reaction scheme:

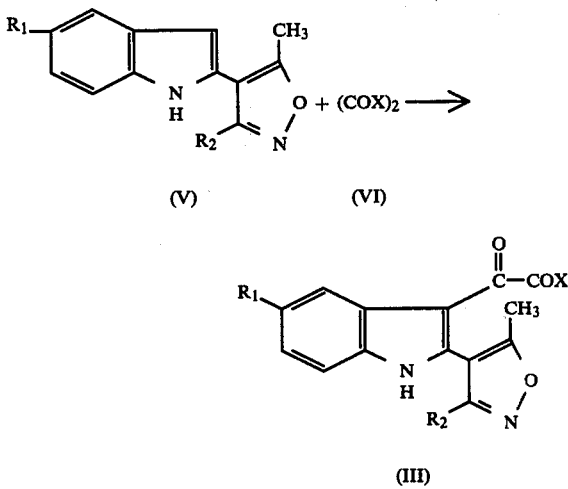

where X, $R_1$ and $R_2$ are as defined above.

The compounds of formula (III) are prepared by treating a compound of the formula (V) with a compound of the formula (VI), namely oxalyl chloride or oxalyl bromide, in the presence of an inert organic solvent. Although the particular solvent employed is not critical, the preferred solvents include an ether such as diethylether, dioxane or tetrahydrofuran, or an aromatic hydrocarbon such as benzene, toluene and the like, preferably diethylether. The temperature of the reaction is not critical, but it is preferred that the reaction be run at a temperature of from about $-10°$ to $50°$ C., preferably from about $20°$ to $30°$ C. The reaction is run from about 1 to 12 hours, preferably from about 3 to 6 hours. The product may be recovered by conventional techniques, however, in this case, it is not isolated instead the compounds of formula (III) are employed in situ as a starting materials in the preparation of compounds (II).

The compounds of formula (V) are prepared in accordance with the following reaction scheme:

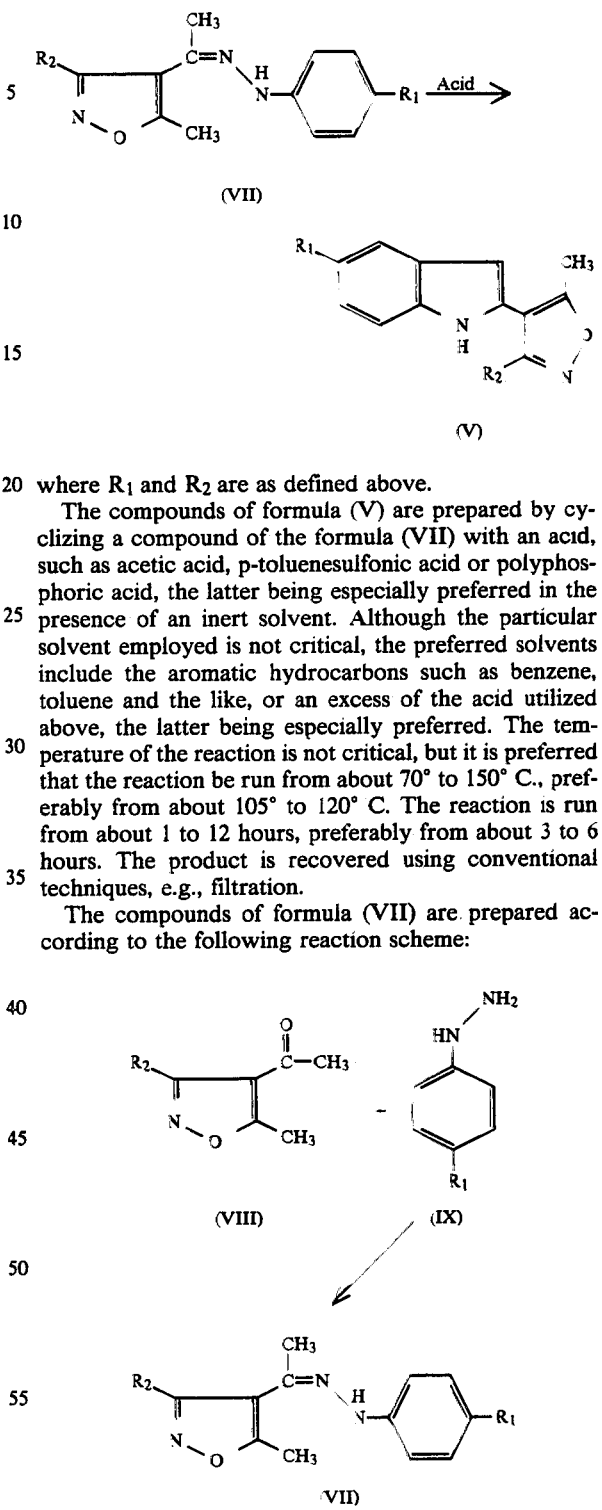

where $R_1$ and $R_2$ are as defined above.

The compounds of formula (V) are prepared by cyclizing a compound of the formula (VII) with an acid, such as acetic acid, p-toluenesulfonic acid or polyphosphoric acid, the latter being especially preferred in the presence of an inert solvent. Although the particular solvent employed is not critical, the preferred solvents include the aromatic hydrocarbons such as benzene, toluene and the like, or an excess of the acid utilized above, the latter being especially preferred. The temperature of the reaction is not critical, but it is preferred that the reaction be run from about $70°$ to $150°$ C., preferably from about $105°$ to $120°$ C. The reaction is run from about 1 to 12 hours, preferably from about 3 to 6 hours. The product is recovered using conventional techniques, e.g., filtration.

The compounds of formula (VII) are prepared according to the following reaction scheme:

where $R_1$ and $R_2$ are as defined above.

The compounds of formula (VII) are prepared by treating a compound of the formula (VIII) with a compound of the formula (IX) in the presence of an inert organic solvent. The particular solvent employed is not critical, but it is preferred that the reaction be run in the presence of the lower alkanols, e.g., methanol, ethanol and the like, or the aromatic hydrocarbons such as benzene, toluene and the like, preferably, however, ethanol. The temperature of the reaction is not critical, but it is preferred that the reaction be run from about 0° to 100° C., preferably from about 20° to 35° C. The reaction is run from about 12 to 72 hours, preferably from about 36 to 52 hours. The product is recovered using conventional techniques, e.g., filtration.

Another aspect of this invention and the preferred method of preparing the compounds of formula (I) in which R₂ represents lower alkyl may be illustrated by the following reaction scheme:

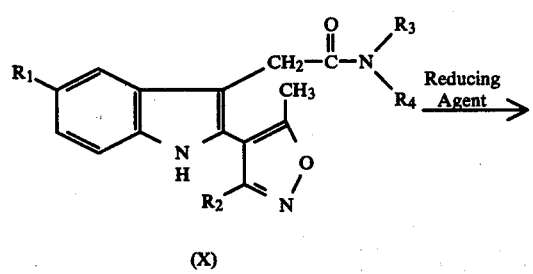

(X)

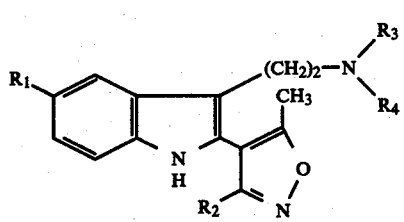

(Ib)

where R₁, R₂ R₃ and R₄ are as defined above.

The compounds of formula (Ib) are prepared by reducing a compound of the formula (X) in the presence of an inert atmosphere, e.g., nitrogen, helium or argon, preferably nitrogen with a reducing agent such as lithium aluminum hydride or diborane, preferably lithium aluminum hydride. The reaction is carried out in the presence of an inert organic solvent and although the particular solvent employed is not critical, the preferred solvents include an ether such as diethylether, dioxane or tetrahydrofuran, the latter being especially preferred. The temperature of the reaction is not critical, but it is preferred that the reaction be run at a temperature of from about 0° to 50° C., preferably from about 20° to 30° C. The reaction is run from about 30 minutes to 5 hours, preferably from about 1 to 3 hours. The product is recovered using conventional techniques, e.g., crystallization.

The compounds of formula (X) are prepared in accordance with the following reaction scheme:

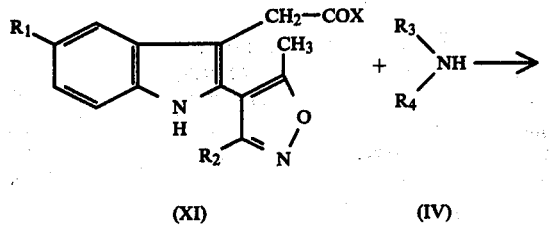

(XI)      (IV)

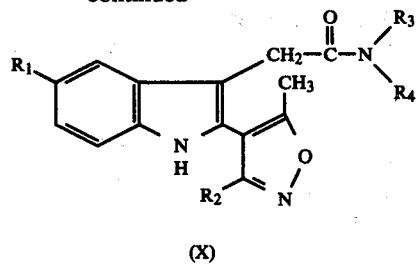

(X)

where X, R₁, R₂, R₃ and R₄ are as defined above.

The compounds of formula (X) are prepared by treating a compound of the formula (XI) with a compound of the formula (IV) in the presence of a solvent. Although the particular solvent employed is not critical, the preferred solvents include water and an excess of a compound of the formula (IV) or an ether such as diethylether, dioxane or tetrahydrofuran, preferably, however, the combination of water and an excess of a compound of the formula (IV), together with tetrahydrofuran. The temperature of the reaction is not critical, but it is preferred that the reaction be run from about 0° to 50° C., preferably from about 20° to 30° C. The reaction is run from about 30 minutes to 5 hours, preferably from about 1 to 3 hours. The product is recovered using conventional techniques, e.g., filtration.

The compounds of formula (XI) are prepared according to the following reaction scheme:

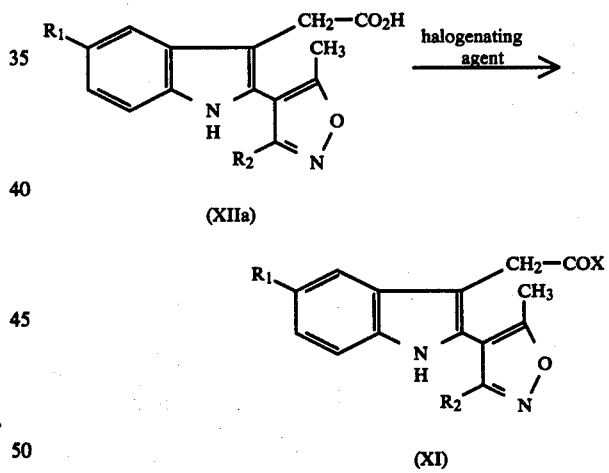

where X, R₁, and R₂ are as defined above.

The compounds of formula (XI) are prepared by reacting a compound of the formula (XIIa) with a halogenating agent in the presence of an inert organic solvent. Although the particular halogenating agent is not critical, the preferred halogenating agents include thionyl chloride, thionyl bromide, phosphorous oxychloride and the like, preferably thionyl chloride. The preferred inert organic solvents include the ethers such as diethylether, dioxane or tetrahydrofuran or the aromatic hydrocarbons such as benzene, toluene and the like, preferably toluene. The temperature of the reaction is not critical but it is preferred that the reaction be run at a temperature of from about 0° to 50° C., preferably from about 20° to 30° C. The reaction is run from about 2 to 24 hours, preferably from about 15 to 20 hours. The product may be recovered by conventional techniques, e.g., evaporation.

The compounds of formula (XIIa) are prepared according to the following reaction scheme:

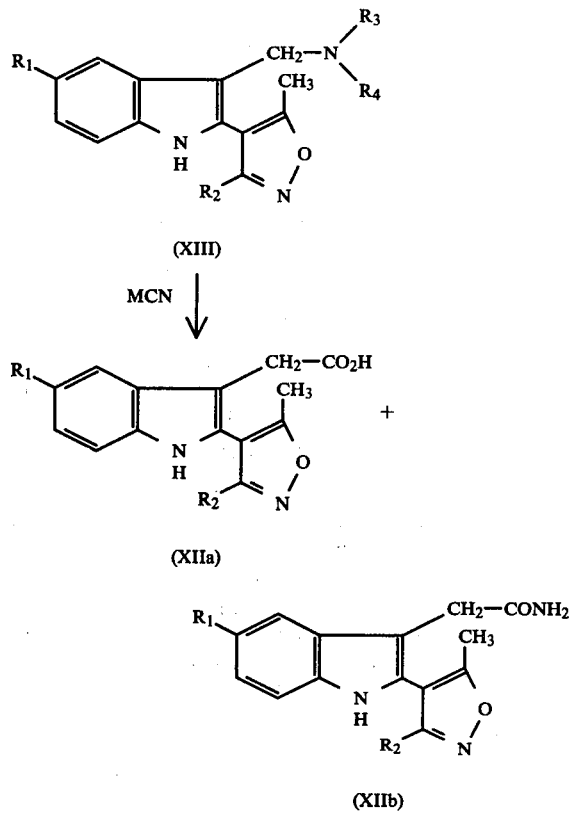

where

M represents an alkali metal such as sodium, potassium and the like, and $R_1$, $R_2$, $R_3$ and $R_4$ are as defined above.

The compounds of formulae (XIIa) and (XIIb) are prepared by treating a compound of the formula (XIII) with an alkali metal cyanide such as sodium cyanide or potassium cyanide, preferably sodium cyanide, in the presence of an aqueous alcoholic solvent. Although the particular aqueous alcoholic solvent employed is not critical, it is preferred that the reaction be run in the presence of the lower alkanols and water, e.g., methanol in water, ethanol in water and the like, preferably ethanol in water. The temperature of the reaction is not critical but it is preferred that the reaction be run at a temperature of from about 80° to 150° C., preferably the reflux temperature of the solvent. The reaction is run from about 50 to 100 hours, preferably from about 70 to 90 hours. The product may be recovered by conventional techniques, e.g., filtration. It should be noted that reacting a compound of the formula (XIII) with an alkali metal cyanide results in a mixture of compounds (XIIa) and (XIIb). Only compounds of the formula (XIIa) are employed to prepare compounds of the formula (XI), although compounds of the formula (XIIb) may be hydrolyzed using conventional techniques to obtain compounds of the formula (XIIa).

The compounds of the formula (XIII) are prepared according to the following reaction scheme:

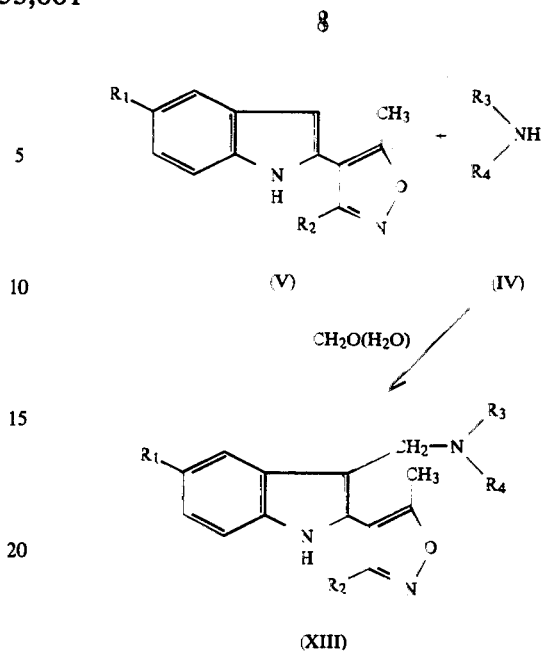

where $R_1$, $R_2$, $R_3$, and $R_4$ are as defined above.

The compounds of formula (XIII) are prepared by reacting a compound of the formula (V) with a compound of the formula (IV) and a formaldehyde solution in the presence of acetic acid and an organic co-solvent. Although the particular co-solvent employed is not critical, it is preferred that the reaction be run in the presence of an ether such as diethyl ether, tetrahydrofuran or dioxane, the latter being especially preferred. The temperature of the reaction is not critical but it is preferred that the reaction be run at a temperature of from about −10° to 30° C., preferably from about 0° to 10° C. The reaction is run from about 30 minutes to 8 hours, preferably from about 1 to 3 hours. The product is recovered using conventional techniques, e.g., crystallization.

Many of the compounds of formulae (IV), (VI), (VIII), and (IX) are known and may be prepared by methods described in the literature. The compounds of formulae (IV), (VI), (VIII), and (IX) not specifically described may be prepared by analogous methods from known starting materials.

The compounds of formula (I), and their pharmaceutically acceptable salts, are useful in the treatment of diabetes particularly as hypoglycemic agents as indicated by Test A; the lowering of blood glucose in 6 to 8 week old male Royal Hart mice weighing 30 to 35 grams which are fasted in groups of 5 for 16 hours and then are given an initial dose of 50 to 200 mg per kilogram of animal body weight of the compound orally. Two hours after the test compound is administered the mice are anesthetized with 85 milligrams per kilogram of animal body weight of sodium hexobarbital and five minutes later blood is collected via cardiac puncture. The blood samples are placed in an autoanalyzer cup containing 0.025 milliliters of heparin (1,000 units per milliliter); and the samples are capped, shaken and stored in ice. The glucose level is determined by the autoanalyzer potassium ferric-cyanide N-26 method and these glucose levels are then compared with the glucose levels of the control group which receives orally 0.5% carboxymethyl cellulose and is run concurrently.

The compounds of formula (I) and their pharmaceutically acceptable salts are also useful in the treatment of diabetes as indicated by Test B; the lowering of blood glucose in male cebus monkeys weighing 1.8 to 3.4 kilograms. After the monkeys were fasted for 16 to 18 hours, they are given orally 10 to 50 mg/kg of test compound suspended in 0.5% carboxymethylcellulose (CMC) solution. The control group receives orally 0.5% carboxymethylcellulose (CMC) solution only. Two blood samples for basal blood sugar level were taken, one 30 minutes before administration of the test compound to the test group and 0.5% CMC to the control group, and the other just prior to administration of the test compound to the test group and 0.5% CMC to the control group. Thereafter, blood samples were taken hourly for six hours. Blood sugar levels were determined by the autoanalyzer potassium ferric-cyanide N-2b method and the glucose levels of the control group were then compared to the test group.

For anti-diabetic use, the compounds of formula (I) and their non-toxic, pharmaceutically acceptable salts may be administered orally or parenterally as such or admixed with conventional pharmaceutical carriers. They may be administered orally in such forms as tablets, dispersible powders, granules, capsules, syrups and elixirs, and parenterally as solutions, e.g., a sterile injectable aqueous solution. The compositions for oral use may contain one of more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., strach and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups, and elixirs may contain the active ingredient in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl-p-hydroxy-benzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination with the carrier or adjuvant.

The anti-diabetic effective amount of active ingredient employed in the treatment of diabetes may vary depending on the particular compound employed, the mode of administration and the severity of the condition being treated. However, in general, satisfactory results in the treatment of diabetes are obtained when a compound of formula (I), or a pharmaceutically acceptable salt thereof, is administered at a daily dosage of from about 5 milligrams to about 400 milligrams per kilogram of animal body weight, preferably given orally and in divided doses two to four times a day, or in sustained release form. For most large mammals, the total daily dosage is from about 50 milligrams to about 2000 milligrams. Unit dosage forms suitable for internal use comprise from about 12.5 milligrams to about 2000 milligrams, more usually 12.5 to 1000 milligrams, of the active compound in intimate admixture with a solid or liquid, pharmaceutically acceptable carrier.

The compounds of formula (I) may be similarly administered in the form of their non-toxic pharmaceutically acceptable acid addition salts. Such salts possess the same order of activity as the free base and are readily prepared by reacting the compound with a pharmaceutically acceptable acid by conventional techniques, and accordingly are included within the scope of this invention. Representative of such salts are the hydrochloride, hydrobromide, hydroiodide, phosphate (including hydrogen phosphate), metaphosphate, and sulfate (including hydrogen sulfate).

Tablets and capsules containing the ingredients indicated below may be prepared by conventional techniques and are useful in treating diabetes, at a dose of one tablet or capsule, 2 to 4 times a day.

| Ingredients | Weight (mg.) tablet | capsule |
|---|---|---|
| 2-(5-methyl-3-phenyl-4-isoxazolyl)-3-(dimethylaminoethyl)-indole | 100 | 100 |
| tragacanth | 10 | — |
| lactose | 247.5 | 300 |
| corn starch | 25 | — |
| talcum | 15 | — |
| magnesium stearate | 2.5 | — |
| Total | 400.0 | 400 |

EXAMPLE 1

1-(5-methyl-3-phenyl-4-isoxazolyl)-1-ethanone phenyl hydrazone

A mixture of 80.4 g. (0.4 mole) of 4-acetyl-5-methyl-3-phenyl isoxazole, 39.4 ml. (0.4 mole) of phenyl hydrazine and 500 mg. toluenesulfonic acid in 400 ml. ethanol is stirred at room temperature for 48 hours. The resulting solid is filtered and washed with cold ether to give 1-(5-methyl-3-phenyl-4-isoxazolyl)-1-ethanone phenyl hydrazone; m.p. 129°–133° C.

Following the above procedure and using in place of phenylhydrazine an equivalent amount of
(a) p-fluorophenyl hydrazine,
(b) p-tolylhydrazine, or
(c) p-anisyl hydrazine
there is obtained
(a) 1-(5-methyl-3-phenyl-4-isoxazolyl)-1-ethanone-p-fluorophenyl hydrazone,
(b) 1-(5-methyl-3-phenyl-4-isoxazolyl)-1-ethanone-p-tolyl hydrazone, or
(c) 1-(5-methyl-3-phenyl-4-isoxazolyl)-1-ethanone-p-anisyl hydrazone, respectively.

EXAMPLE 2

2-(5-methyl-3-phenyl-4-isoxazolyl)-indole

To 1350 grams of polyphosphoric acid at 100° to 110° C., there is added portionwise 89.3 g. (0.307 mole) of 1-(5-methyl-3-phenyl-4-isoxazolyl)-1-ethanone phenyl hydrazone, while maintaining the temperature between 105° and 115° C. After addition is complete the mixture is stirred at 100° to 110° C. for 3 hours. The mixture is then poured onto ice and water and the resulting solid is filtered and washed with water. The solid is then dissolved in ether, washed with water, dried and evaporated partially and cooled in ice. The resulting solid is filtered and washed with cold ether to give 2-(5-methyl-3-phenyl-4-isoxazolyl)-indole; m.p. 145° to 146° C.

Following the above procedure and using in place of 1-(5-methyl-3-phenyl-4-isoxazolyl)-1-ethanone phenyl hydrazone an equivalent amount of (a) 1-(5-methyl-3-phenyl-4-isoxazolyl)-1-ethanone-p-fluorophenyl hydrazone, (b) 1-(5-methyl-3-phenyl-4-isoxazolyl)-1-ethanone-p-tolyl hydrazone, or (c) 1-(5-methyl-3-phenyl-4-isoxazolyl)-1-ethanone-p-anisyl hydrazone there is obtained (a) 5-fluoro-2-(5-methyl-3-phenyl-4-isoxazolyl)-indole, (b) 5-methyl-2-(5-methyl-3-phenyl-4-isoxazolyl)-indole, or (c) 5-methoxy-2-(5-methyl-3-phenyl-4-isoxazolyl)-indole, respectively.

EXAMPLE 3

2-(5-methyl-3-phenyl-4-isoxazolyl)-3-indoleglyoxylchloride

A mixture of 197.6 g. (0.72 mole) of 2-(5-methyl-3-phenyl-4-isoxazolyl)-indole and 3 liters of ether is cooled to 0° to 10° C. and 61.6 ml. (0.72 mole) of oxalyl chloride in 450 ml. of ether is added dropwise, maintaining the temperature at 0° to 10° C. during the addition. The cooling bath is removed and the mixture allowed to warm to room temperature. After 1½ hours, some starting material is still present and 3.1 ml. (0.0362 mole) of oxalyl chloride is added and the mixture stirred for additional 1½ hours longer. Total stirring at room temperature is 3 hours. The solvent is evaporated in vacuo to give a solid residue. The residue is suspended in ether and evaporated twice more to give 2-(5-methyl-3-phenyl-4-isoxazolyl)-3-indoleglyoxyl chloride.

Following the above procedure and using in place of 2-(5-methyl-3-phenyl-4-isoxazolyl)-indole an equivalent amount of (a) 5-fluoro-2-(5-methyl-3-phenyl-4-isoxazolyl)-indole, (b) 5-methyl-2-(5-methyl-3-phenyl-4-isoxazolyl)-indole, or (c) 5-methoxy-2-(5-methyl-3-phenyl-4-isoxazolyl)-indole there is obtained (a) 5-fluoro-2-(5-methyl-3-phenyl-4-isoxazolyl)-3-indoleglyoxylchloride, (b) 5-methyl-2-(5-methyl-3-phenyl-4-isoxazolyl)-3-indoleglyoxylchloride, or (c) 5-methoxy-2-(5-methyl-3-phenyl-4-isoxazolyl)-3-indoleglyoxylchloride, respectively.

EXAMPLE 4

N,N-dimethyl-2-(5-methyl-3-phenyl-4-isoxazolyl)-3-indoleglyoxylamide 91.0 g. (0.250 mole) of 2-(5-methyl-3-phenyl-4-isoxazolyl)-3-indoleglyoxylchloride is added portionwise to a 0° to 10° C. cooled mixture of 1200 ml. of 40% aqueous dimethylamine and 1000 ml. of ether. The resulting mixture is stirred for 1 hour without an ice bath and then filtered. The solid is then washed well with water and with three portions of cold ether to give N,N-dimethyl-2-(5-methyl-3-phenyl-4-isoxazolyl)-3-indoleglyoxylamide; m.p. 258.5° to 260.5° C.

Following the above procedure and using in place of 2-(5-methyl-3-phenyl-4-isoxazolyl)-3-indoleglyoxylchloride, an equivalent amount of (a) 5-fluoro-2-(5-methyl-3-phenyl-4-isoxazolyl)-3-indoleglyoxylchloride, (b) 5-methyl-2-(5-methyl-3-phenyl-4-isoxazolyl)-3-indoleglyoxylchloride, or (c) 5-methoxy-2-(5-methyl-3-phenyl-4-isoxazolyl)-3-indoleglyoxylchloride there is obtained (a) 5-fluoro-N,N-dimethyl-2-(5-methyl-3-phenyl-4-isoxazolyl)-3-indoleglyoxylamide, (b) 5-methyl-N,N-dimethyl-2-(5-methyl-3-phenyl-4-isoxazolyl)-3-indoleglyoxylamide, or (c) 5-methoxy-N,N-dimethyl-2-(5-methyl-3-phenyl-4-isoxazolyl)-3-indoleglyoxylamide, respectively.

Also following the above procedure and using in place of dimethylamine an equivalent amount of (d) morpholine, (e) piperidine, or (f) N-methylpiperazine there is obtained (d) 2-(5-methyl-3-phenyl-4-isoxazolyl)-3-indoleglyoxylmorpholide, (e) 2-(5-methyl-3-phenyl-4-isoxazolyl)-3-indoleglyoxylpiperidide, or (f) 2-(5-methyl-3-phenyl-4-isoxazolyl)-3-indoleglyoxyl-4-methyl-piperazide, respectively.

EXAMPLE 5

2-(5-methyl-3-phenyl-4-isoxazolyl)-3-(dimethylaminoethyl)-indole

To a refluxing suspension of 22.8 g. (0.60 mole) of lithium aluminum hydride in 1100 ml. of tetrahydrofuran under nitrogen, there is added dropwise over approximately 1 to 1½ hours a warm solution of 56 g. (0.15 mole) of N,N-dimethyl-2-(5-methyl-3-phenyl-4-isoxazolyl)-3-indoleglyoxylamide in 2250 ml. of tetrahydrofuran. The mixture is refluxed for 3 hours after addition is completed. The resulting suspension is cooled to −10° to +5° C. and a solution of 270 ml. of tetrahydrofuran and 90 ml. of water is added dropwise with the temperature maintained between −10° and +5° C. The suspension is stirred for approximately 1 hour without a cooling bath and then allowed to stand overnight without stirring. The mixture is filtered, the filtrate evaporated in vacuo and the residue dissolved in methylene chloride. The methylene chloride is washed with water, dried and evaporated in vacuo. The residue is crystallized from ether to give 2-(5-methyl-3-phenyl-4-isoxazolyl)-3-(dimethylaminoethyl)-indole; m.p. 141.5° to 143.5° C.

Following the above procedure and using in place of N,N-dimethyl-2-(5-methyl-3-phenyl-4-isoxazolyl)-3-indoleglyoxylamide an equivalent amount of (a) 5-fluoro-N,N-dimethyl-2-(5-methyl-3-phenyl-4-isoxazolyl)-3-indoleglyoxylamide, (b) 5-methyl-N,N-dimethyl-2-(5-methyl-3-phenyl-4-isoxazolyl)-3-indoleglyoxylamide, (c) 5-methoxy-N,N-dimethyl-2-(5-methyl-3-phenyl-4-isoxazolyl)-3-indoleglyoxylamide, (d) 2-(5-methyl-3-phenyl-4-isoxazolyl)-3-indoleglyoxylmorpholide, (e) 2-(5-methyl-3-phenyl-4-isoxazolyl)-3-indoleglyoxylpiperidide, or (f) 2-(5-methyl-3-phenyl-4-isoxazolyl)-3-indoleglyoxyl-4-methyl-piperazide, there is obtained
(a) 5-fluoro-2-(5-methyl-3-phenyl-4-isoxazolyl)-3-(dimethylaminoethyl)-indole,
(b) 5-methyl-2-(5-methyl-3-phenyl-4-isoxazolyl)-3-(dimethylaminoethyl)-indole,
(c) 5-methoxy-2-(5-methyl-3-phenyl-4-isoxazolyl)-3-(dimethylaminoethyl)-indole,
(d) 2-(5-methyl-3-phenyl-4-isoxazolyl)-3-(morpholinoethyl)-indole,
(e) 2-(5-methyl-3-phenyl-4-isoxazolyl)-3-(piperidinoethyl)-indole, or
(f) 2-(5-methyl-3-phenyl-4-isoxazolyl)-3-(4-methyl-piperazinoethyl)-indole, respectively.

The 2-(5-methyl-3-phenyl-4-isoxazolyl)-3-(dimethylaminoethyl)-indole of this example is an effective anti-diabetic agent at a dosage of 100 mg. two to four times a day.

The title compound of the example has an $ED_{25}$ in Test A of 160.0 mg/kg p.o. and an $ED_{25}$ in Test B of 20.0 mg/kg p.o.

EXAMPLE 6

A preferred process for preparing compounds of formula (I) wherein $R_2$ represents lower alkyl, in particular a 2-(3-ethyl-5-methyl-4-isoxazolyl)-3-(dimethylaminoethyl)-indole

Step (A).

2-(3-ethyl-5-methyl-4-isoxazolyl)-3-(dimethylaminomethyl)-indole

A mixture of 20.6 ml. (0.24 mole) 37% aqueous formaldehyde, 18 ml. (0.12 mole) 40% aqueous dimethylamine and 80 ml. acetic acid is cooled to 0° and treated by the dropwise addition of 25.5 g. (0.113 mole) 2-(3-ethyl-5-methyl-4-isoxazolyl)-indole in a solution of 45 ml. acetic acid and 125 ml. dioxane. After addition is complete the mixture is stirred for 1 hour at room temperature and poured onto 500 ml. ice-water. The resulting solution is made basic with 20% potassium hydroxide and then extracted with methylene chloride. The methylene chloride is washed with water, brine, dried over anhydrous magnesium sulfate, filtered and evaporated to give a gum that crystallizes to give 2-(3-ethyl-5-methyl-4-isoxazolyl)-3-(dimethylaminomethyl)-indole; m.p. 88° to 90° C.

Step (b).

2-(3-ethyl-5-methyl-4-isoxazolyl)-3-indole acetic acid

A mixture of 24.8 g. (0.088 mole) of 2-(3-ethyl-5-methyl-4-isoxazolyl)-3-(dimethylaminomethyl)-indole and 23 g. (0.47 mole) of sodium cyanide in 175 ml. ethanol and 50 ml. water are refluxed for 80 hours. The mixture is then cooled and poured onto water, stirred for ½ hour and filtered to yield 2-(3-ethyl-5-methyl-4-isoxazolyl)-3-indole acetamide; m.p. 194° to 195° C. The filtrate, which contains the sodium salt of 2-(3-ethyl-5-methyl-4-isoxazolyl)-3-indole acetic acid is evaporated to remove ethanol and acidified with cold 12 N hydrochloric acid and the precipitate filtered to give 2-(3-ethyl-5-methyl-4-isoxazolyl)-3-indole acetic acid; m.p. 194° to 197° C.

Step (c).

2-(3-ethyl-5-methyl-4-isoxazolyl)-3-indole acetyl chloride

A mixture of 10.3 g. (0.036 mole) 2-(3-ethyl-5-methyl-4-isoxazolyl)-3-indole acetic acid and 22.0 g. (0.185 mole) thionyl chloride in 100 ml. toluene is stirred at room temperature for 18 hours. The toluene is removed in vacuo to give 2-(3-ethyl-5-methyl-4-isoxazolyl)-3-indole acetyl chloride.

Step (d).

N,N-dimethyl-2-(3-ethyl-5-methyl-4-isoxazolyl)-3-indoleacetamide

A mixture of 11.2 g. (0.036 mole) of 2-(3-ethyl-5-methyl-4-isoxazolyl)-3-indole acetyl chloride in 100 ml. of tetrahydrofuran is added to a vigorously stirred solution of dimethylamine in water (25 ml. 40% dimethylamine in water) at 0° to 10° C. The resulting mixture is allowed to warm to room temperature and poured into ether-water. The organic layer is separated, dried over anhydrous magnesium sulfate, filtered and evaporated to give N,N-dimethyl-2-(3-ethyl-5-methyl-4-isoxazolyl)-3-indole acetamide; m.p. 176° to 178° C.

Step (e).

2-(3-ethyl-5-methyl-4-isoxazolyl)-3-dimethylaminoethyl)-indole

A solution of 4.7 g. (0.015 mole) of N,N-dimethyl-2-(3-ethyl-5-methyl-4-isoxazolyl)-3-indoleacetamide in 47 ml. of tetrahydrofuran under nitrogen is added dropwise to a suspension of 2.28 g. (0.06 mole) lithium aluminum hydride in 50 ml. tetrahydrofuran, while maintaining the reaction at room temperature. The mixture is stirred for 1½ hours at room temperature, cooled in ice and quenched with 5 ml. water in 50 ml. tetrahydrofuran. The resulting solids are filtered and the filtrate dried over anhydrous magnesium sulfate, filtered and evaporated and the residue crystallized from ether to give 2-(3-ethyl-5-methyl-4-isoxazolyl)-3-(dimethylaminoethyl)-indole; m.p. 118° to 120° C.

What is claimed is:

1. A compound of the formula

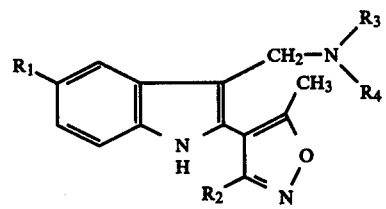

wherein
$R_1$ represents hydrogen, fluoro, chloro, lower alkyl having 1 to 4 carbon atoms, or lower alkoxy having 1 to 4 carbon atoms,
$R_2$ represents lower alkyl having 1 to 4 carbon atoms, or

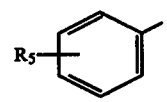

where $R_5$ represents hydrogen, fluoro, chloro, lower alkyl as defined above or lower alkoxy as defined above, and $R_3$ and $R_4$ each independently represent lower alkyl as defined above, or $R_3$ and $R_4$ together with N represent

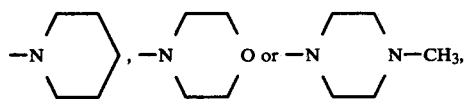

or a pharmaceutically acceptable acid addition salt thereof.

2. A compound of the formula

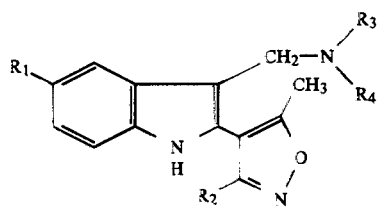

wherein $R_1$ represents hydrogen, fluoro, chloro, lower alkyl having 1 to 4 carbon atoms, or lower alkoxy having 1 to 4 carbon atoms, $R_2$ represents lower alkyl having 1 to 4 carbon atoms, and $R_3$ and $R_4$ each independently represent lower alkyl having 1 to 4 carbon atoms, or a pharmaceutically acceptable acid addition salt thereof.

3. The compound of claim 2, which is 2-(3-ethyl-5-methyl-4-isoxazolyl)-3-(dimethylaminomethyl)-indole.

* * * * *